United States Patent
Lewis et al.

(10) Patent No.: US 9,339,481 B2
(45) Date of Patent: *May 17, 2016

(54) PHOSPHATE-BINDING MAGNESIUM SALTS AND USES THEREOF

(71) Applicant: PERNIX THERAPEUTICS HOLDINGS, INC., Magnolia, TX (US)

(72) Inventors: Robert L. Lewis, Madison, MS (US); Charles E. Day, Leitchfield, KY (US)

(73) Assignee: Cypress Pharmaceuticals, Inc., Morristown, NJ (US)

( * ) Notice: Subject to any disclaimer, the term of this patent is extended or adjusted under 35 U.S.C. 154(b) by 423 days.

This patent is subject to a terminal disclaimer.

(21) Appl. No.: 13/856,084

(22) Filed: Apr. 3, 2013

(65) Prior Publication Data
US 2014/0010877 A1    Jan. 9, 2014

Related U.S. Application Data

(63) Continuation of application No. 13/544,949, filed on Jul. 9, 2012, now abandoned, which is a continuation of application No. 12/422,012, filed on Apr. 10, 2009, now Pat. No. 8,247,000.

(51) Int. Cl.
| | |
|---|---|
| *A61K 33/06* | (2006.01) |
| *A61K 31/19* | (2006.01) |
| *A61K 31/715* | (2006.01) |
| *A61K 33/08* | (2006.01) |
| *A61K 33/10* | (2006.01) |
| *A61K 31/197* | (2006.01) |
| *A61K 9/28* | (2006.01) |
| *A61K 9/48* | (2006.01) |

(52) U.S. Cl.
CPC .............. *A61K 31/19* (2013.01); *A61K 31/197* (2013.01); *A61K 31/715* (2013.01); *A61K 33/06* (2013.01); *A61K 33/08* (2013.01); *A61K 33/10* (2013.01); *A61K 9/2806* (2013.01); *A61K 9/4891* (2013.01)

(58) Field of Classification Search
CPC .................................................... A61K 31/36
See application file for complete search history.

(56) References Cited

U.S. PATENT DOCUMENTS

| | | |
|---|---|---|
| 2003/0147995 A1 | 8/2003 | Koss et al. |
| 2003/0206969 A1 | 11/2003 | Nidamarty et al. |
| 2005/0214383 A1 | 9/2005 | Bubnis et al. |
| 2008/0318924 A1 | 12/2008 | Matsushima et al. |

FOREIGN PATENT DOCUMENTS

| | | |
|---|---|---|
| DE | 29910454 U1 | 9/1999 |
| JP | 2008-069173 | 3/2008 |
| WO | WO 99/15189 | 4/1999 |
| WO | WO-2007/056405 A2 | 5/2007 |
| WO | WO-2008/116215 A2 | 9/2008 |
| WO | WO-2008/116226 | 9/2008 |

OTHER PUBLICATIONS

Guillot, et al., "The Use of Magnesium-Containing Phosphate Binders in Patients with End-Stage Renal Disease on Maintenance Hemodialysis", Nephron, vol. 30, No. 2, pp. 114-117 (1982).
Deuber H. J., "Kombinierter Einsatz von Kalziumazetat and Magnesiumkarbonat als orale Phosphatbinder", vol. 33, No. 8, pp. 403-408, 2004.
International Search Report for International Application No. PCT/US09/40213, mailed Dec. 21, 2009.
Lowry and Lopez, "The determination of inorganic phosphate in the presence of labile phosphate esters", *J. Biol. Chem.*, 162:421-428 (1946).
Rosenbaum, et al "Effect of RenaGel®, a non-absorbable, corsslinked, polymeric phosphate binder, on urinary phosphorus excretion in rats", *Nephrol. Dial. Transplant*, 12:961-964 (1997).
Written Opinion of the International Search Authority for International Patent Application No. PCT/US09/40213, mailed Dec. 21, 2009.

*Primary Examiner* — Benjamin Packard
(74) *Attorney, Agent, or Firm* — Servilla Whitney LLC

(57) ABSTRACT

The present invention provides, among other things, compositions and methods suitable for the treatment of hyperphosphatemia based on phosphate-binding magnesium salts. In some embodiments, the present invention provides compositions and methods suitable for the treatment of hyperphosphatemia based on the combination of phosphate-binding magnesium and calcium salts.

24 Claims, No Drawings

PHOSPHATE-BINDING MAGNESIUM SALTS AND USES THEREOF

CROSS-REFERENCE TO RELATED APPLICATIONS

This application is a continuation of prior application Ser. No. 13/544,949, filed on Jul. 9, 2012, now abandoned, which is a continuation of prior application Ser. No. 12/422,012, filed on Apr. 10, 2009, now U.S. Pat. No. 8,247,000, which are hereby incorporated by reference in their entirety.

BACKGROUND OF THE INVENTION

Like other diseases for which there is no cure, chronic kidney disease takes an ever-increasing toll on patients who have it. As the disease progresses, the kidney becomes less efficient at removing various ions from the blood. Among these ions is phosphate, which can form insoluble particles when combined with calcium. In end-stage renal disease, the final stage of chronic kidney disease, kidney function is so compromised that phosphate levels in the blood (serum) become markedly elevated. This condition, known as hyperphosphatemia, carries with it many grave health risks. For example, when serum phosphate and calcium levels are above a certain threshold, hardened deposits may form throughout the body, endangering circulation. It is therefore very important to control serum phosphate levels in patients with end-stage renal disease.

Patients with end-stage renal disease may be advised to eat a diet low in phosphate. However, phosphate is present at some level in almost all the foods we eat. For this reason, phosphate binders were developed. Phosphate binders are compounds taken orally and which act in the gastrointestinal tract to bind phosphate and keep it from being absorbed. Phosphate binders are generally taken with each meal. Phosphate binders known in the art include, for example, various salts of aluminum and calcium, as well as some chemically synthesized crosslinked polymers. There are clinical circumstances in which the administration of aluminum or calcium salts is ill-advised. In animal models, certain crosslinked polymers carry with them elevated risks of carcinogenesis. Therefore, there is a need for safer and more effective phosphate binders.

SUMMARY OF THE INVENTION

The present invention encompasses the discovery that certain magnesium salts are surprisingly effective in phosphate binding. Thus, the present invention provides therapeutic compositions and methods for removing phosphate from a mammalian subject based on one or more phosphate-binding magnesium salts. Among other things, phosphate-binding magnesium salts of the invention are particularly useful when they are used in combination with other phosphate-binders (e.g., calcium salts) in treating hyperphosphatemia. For example, a combination of a magnesium salt with a calcium salt may provide effective phosphate-binding while reducing the total dose of calcium and, at the same time, providing better nutritional balance. Therefore, the present invention provides phosphate-binding compositions and methods that are safer and more effective.

In one aspect, the present invention provides a composition suitable for treating hyperphosphatemia comprising a therapeutically effective dose of at least one calcium salt and at least one phosphate-binding magnesium salt. In some embodiments, the at least one phosphate-binding magnesium salt binds at least about 50 mg phosphate per gram magnesium salt.

In some embodiments, the therapeutically effective dose of at least one calcium salt contains about 20 mg to 1200 mg of calcium. In some embodiments, the therapeutically effective dose of at least one calcium salt contains less than about 2000 mg (e.g., less than about 1800 mg, less than about 1600 mg, less than about 1400 mg, less than about 1200 mg, less than about 1000 mg, less than about 800 mg, less than about 600 mg, less than about 400 mg, less than about 200) of calcium.

In some embodiments, the therapeutically effective dose of at least one phosphate-binding magnesium salt contains about 20 mg to 1200 mg magnesium. In some embodiments, the therapeutically effective dose of at least one phosphate-binding magnesium salt comprises less than about 1200 mg magnesium.

In some embodiments, the at least one calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium camitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combination thereof.

In some embodiments, the at least one phosphate-binding magnesium salt is selected from the group consisting of magnesium aminobutyrate, magnesium arginate, magnesium aspartate, magnesium betainate, magnesium carnitinate, magnesium glycinate, magnesium hydroxide, magnesium lysinate, magnesium oxide, magnesium propionate, and combination thereof.

In some embodiments, the mass ratio of the at least one calcium salt to the at least one phosphate-binding magnesium salt is between about 100:1 and about 1:100. In some embodiments, the mass ratio of the at least one calcium salt to the at least one phosphate-binding magnesium salt is between about 10:1 and about 1:10. In some embodiments, the mass ratio of the at least one calcium salt to the at least one phosphate-binding magnesium salt is between about 3:1 and about 1:3. In some embodiments, the mass ratio of the at least one calcium salt to the at least one phosphate-binding magnesium salt is between about 2:1 and about 1:2. In some embodiments, the mass ratio of the at least one calcium salt to the at least one phosphate-binding magnesium salt is between about 3:2 and about 2:3. In some embodiments, the mass ratio of the at least one calcium salt to the at least one phosphate-binding magnesium salt is between about 5:4 and about 4:5. In some embodiments, the mass ratio of the at least one calcium salt to the at least one phosphate-binding magnesium salt is about 1:1. In some embodiments, the mass ratio of the at least one calcium salt to the at least one phosphate-binding magnesium salt is about 10:9.

In some embodiments, the at least one calcium salt comprises calcium acetate, and the at least one magnesium salt comprises magnesium glycinate.

In some embodiments, the therapeutically effective dose of calcium acetate is about 340 mg and the therapeutically effective dose of magnesium glycinate is about 300 mg.

In another aspect, the present invention provides a composition suitable for treating hyperphosphatemia containing a therapeutically effective dose of at least one phosphate-binding magnesium salt, wherein the at least one phosphate-binding magnesium salt binds at least about 50 mg (e.g., at least about 75 mg, 100 mg, 125 mg, 150 mg, 175 mg) phosphate per gram. In some embodiments, the at least one phosphate-binding magnesium salt binds at least about 100 mg phosphate per gram.

In yet another aspect, the present invention provides a composition suitable for treating hyperphosphatemia containing a therapeutically effective dose of at least one phosphate-binding magnesium salt, wherein the at least one phosphate-binding magnesium salt is not magnesium carbonate. In some embodiments, the at least one phosphate-binding magnesium salt binds at least about 50 mg (e.g., at least about 75 mg, 100 mg, 125 mg, 150 mg, 175 mg) phosphate per gram.

In some embodiments, the at least one phosphate-binding magnesium salt is selected from the group consisting of magnesium aminobutyrate, magnesium arginate, magnesium aspartate, magnesium betainate, magnesium carnitinate, magnesium glycinate, magnesium hydroxide, magnesium lysinate, magnesium oxide, magnesium propionate, and combination thereof.

In some embodiments, the therapeutically effective dose of at least one phosphate-binding magnesium salt contains about 20 mg to 1200 mg magnesium. In some embodiments, the therapeutically effective dose of at least one phosphate-binding magnesium salt contains less than about 1200 mg magnesium.

In some embodiments, the composition further contains a calcium salt. In some embodiments, the calcium salt is present in an amount that provides about 20 mg to 1200 mg calcium. In some embodiments, the calcium salt is present in an amount that provides less than 2000 mg calcium. In some embodiments, the calcium salt is present in an amount that provides less than 600 mg calcium.

In still another aspect, the present invention provides a composition suitable for treating hyperphosphatemia consisting essentially of a calcium salt and a phosphate-binding magnesium salt. In some embodiments, the calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium carnitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combination thereof. In some embodiments, the phosphate-binding magnesium salt is selected from the group consisting of magnesium aminobutyrate, magnesium arginate, magnesium aspartate, magnesium betainate, magnesium carnitinate, magnesium glycinate, magnesium hydroxide, magnesium lysinate, magnesium oxide, magnesium propionate, and combination thereof. In some embodiments, the calcium salt is calcium acetate, and the phosphate-binding magnesium salt is magnesium glycinate.

In some embodiments, the mass ratio of the calcium salt to the phosphate-binding magnesium salt is between about 100:1 and about 1:100. In some embodiments, the mass ratio of the calcium salt to the phosphate-binding magnesium salt is between about 10:1 and about 1:10. In some embodiments, the mass ratio of the calcium salt to the phosphate-binding magnesium salt is between about 3:1 and about 1:3. In some embodiments, the mass ratio of the calcium salt to the phosphate-binding magnesium salt is between about 2:1 and about 1:2. In some embodiments, the mass ratio of the calcium salt to the phosphate-binding magnesium salt is between about 3:2 and about 2:3. In some embodiments, the mass ratio of the calcium salt to the phosphate-binding magnesium salt is between about 5:4 and about 4:5. In some embodiments, the mass ratio of the calcium salt to the phosphate-binding magnesium salt is about 1:1. In some embodiments, the mass ratio of the calcium salt to the phosphate-binding magnesium salt is about 10:9.

In some embodiments, the phosphate-binding magnesium salt is present in an amount that provides about 20 mg to 1200 mg magnesium. In some embodiments, the phosphate-binding magnesium salt is present in an amount that provides less than 1200 mg magnesium. In some embodiments, the calcium salt is present in an amount that provides about 20 mg to 1200 mg calcium. In some embodiments, the calcium salt is present in an amount that provides less than 2000 mg (e.g., less than about 1800 mg, less than about 1600 mg, less than about 1400 mg, less than about 1200 mg, less than about 1000 mg, less than about 800 mg, less than about 600 mg, less than about 400 mg, less than about 200 mg) calcium.

Inventive compositions according to the invention can be formulated for oral administration. In some embodiments, inventive compositions are formulated as a nutritional supplement. In some embodiments, inventive compositions of the invention can be in a form of a tablet, a cachet, a hard gelatin capsule, a soft gelatin capsule, a lozenge, suspension, or a bead.

In some embodiments, inventive compositions further contain an enteric coating. In some embodiments, the enteric coating contains acetyltributyl citrate, carbomers, cellulose acetate phthalate, cellulose acetate succinate, ethyl cellulose, guar gum, hypromellose acetate succinate, hypromellose phthalate, polymethacrylates, polyvinyl acetate phthalate, shellac, tributyl citrate, triethyl citrate, white wax and/or zein In some embodiments, compositions of the invention further include one or more pharmaceutically acceptable excipients. In some embodiments, pharmaceutically acceptable excipients suitable for the invention include starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone and/or talc.

The present invention further provides methods of treating hyperphosphatemia by administering to a subject in need of treatment any one of the compositions described herein.

In one aspect, the present invention provides a method of treating hyperphosphatemia comprising administering to a subject in need of treatment a calcium salt and a phosphate-binding magnesium salt. In some embodiments, the phosphate-binding magnesium salt binds at least about 50 mg phosphate per gram. In some embodiments, the phosphate-binding magnesium salt is not magnesium carbonate.

In some embodiments, the calcium salt is administered in an amount that provides about 20 mg to 1200 mg of calcium per dose. In some embodiments, the calcium salt is administered in an amount that provides less than about 600 mg calcium per dose. In some embodiments, the calcium salt is administered in an amount that provides less than about 2000 mg (e.g., less than about 1800 mg, less than about 1600 mg, less than about 1400 mg, less than about 1200 mg, less than about 1000 mg, less than about 800 mg, less than about 600 mg, less than about 400 mg, less than about 200 mg) calcium per day.

In some embodiments, the phosphate-binding magnesium salt is administered in an amount that provides about 20 mg to 1200 mg magnesium per dose. In some embodiments, the phosphate-binding magnesium salt is administered in an amount that provides less than about 1200 mg magnesium per dose. In some embodiments, the phosphate-binding magnesium salt is administered in an amount that provides less than about 4000 mg (e.g., less than about 3500 mg, less than about 3000 mg, less than about 2500 mg, less than about 2000 mg, less than about 1500 mg, or less than about 1000 mg) magnesium per day.

In some embodiments, the calcium salt and phosphate-binding magnesium salt are administered four times a day. In some embodiments, the calcium salt and phosphate-binding magnesium salt are administered three times a day. In some embodiments, the calcium salt and phosphate-binding magnesium salt are administered twice a day. In some embodiments, the calcium salt and phosphate-binding magnesium salt are administered once daily.

In some embodiments, the calcium salt and phosphate-binding magnesium salt are administered orally.

In some embodiments, the phosphate-binding magnesium salt is administered with an enteric coating. In some embodiments, the enteric coating contains acetyltributyl citrate, carbomers, cellulose acetate phthalate, cellulose acetate succinate, ethyl cellulose, guar gum, hypromellose acetate succinate, hypromellose phthalate, polymethacrylates, polyvinyl acetate phthalate, shellac, tributyl citrate, triethyl citrate, white wax and/or zein.

In some embodiments, the calcium salt and phosphate-binding magnesium salt are administered simultaneously. In some embodiments, the calcium salt and phosphate-binding magnesium salt are administered sequentially.

In some embodiments, the calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium carnitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combination thereof.

In some embodiments, the phosphate-binding magnesium salt is selected from the group consisting of magnesium aminobutyrate, magnesium arginate, magnesium aspartate, magnesium betainate, magnesium carnitinate, magnesium glycinate, magnesium hydroxide, magnesium lysinate, magnesium oxide, magnesium propionate, and combination thereof.

In some embodiments, the calcium salt and phosphate-binding magnesium salt are administered at a mass ratio between about 100:1 and about 1:100. In some embodiments, the calcium salt and phosphate-binding magnesium salt are administered at a mass ratio between about 10:1 and about 1:10. In some embodiments, the calcium salt and phosphate-binding magnesium salt are administered at a mass ratio between about 3:1 and about 1:3. In some embodiments, the calcium salt and phosphate-binding magnesium salt are administered at a mass ratio between about 2:1 and about 1:2. In some embodiments, the calcium salt and phosphate-binding magnesium salt are administered at a mass ratio between about 3:2 and about 2:3. In some embodiments, the calcium salt and phosphate-binding magnesium salt are administered at a mass ratio between about 5:4 and about 4:5. In some embodiments, the calcium salt and phosphate-binding magnesium salt are administered at a mass ratio of about 1:1. In some embodiments, the calcium salt and phosphate-binding magnesium salt are administered at a mass ratio of about 10:9.

In some embodiments, the calcium salt is calcium acetate, and the phosphate-binding magnesium salt is magnesium glycinate. In some embodiments, the calcium acetate is administered at a dose of about 340 mg and the magnesium glycinate is administered at a dose of about 300 mg.

In yet another aspect, the present invention provides a method of treating hyperphosphatemia by administering to a subject in need of treatment a phosphate-binding magnesium salt, wherein the phosphate-binding magnesium salt binds at least about 50 mg phosphate per gram.

In still another aspect, the present invention provides a method of treating hyperphosphatemia by administering to a subject in need of treatment a phosphate-binding magnesium salt, wherein the phosphate-binding magnesium salt is not magnesium carbonate.

In some embodiments, the phosphate-binding magnesium salt is administered in an amount that provides about 20 mg to 1200 mg magnesium per dose. In some embodiment, the phosphate-binding magnesium salt is administered in an amount that provides less than about 1200 mg magnesium per dose. In some embodiments, the phosphate-binding magnesium salt is administered in an amount that provides less than about 4000 mg (e.g., less than about 3500 mg, less than about 3000 mg, less than about 2500 mg, less than about 2000 mg, less than about 1500 mg, or less than about 1000 mg) magnesium per day.

In some embodiments, the phosphate-binding magnesium salt is administered four times a day. In some embodiments, the phosphate-binding magnesium salt is administered three times a day. In some embodiments, the phosphate-binding magnesium salt is administered twice a day. In some embodiments, the phosphate-binding magnesium salt is administered once daily.

In some embodiments, the phosphate-binding magnesium salt is administered orally. In some embodiments, the phosphate-binding magnesium salt is administered in a form of a tablet, a cachet, a hard gelatin capsule, a soft gelatin capsule, a lozenge, suspension, or a bead.

In some embodiments, the phosphate-binding magnesium salt is administered with an enteric coating. In some embodiments, a suitable enteric coating contains acetyltributyl citrate, carbomers, cellulose acetate phthalate, cellulose acetate succinate, ethyl cellulose, guar gum, hypromellose acetate succinate, hypromellose phthalate, polymethacrylates, polyvinyl acetate phthalate, shellac, tributyl citrate, triethyl citrate, white wax and/or zein.

In some embodiments, the phosphate-binding magnesium salt is administered in combination with another phosphate binder (e.g., a calcium salt).

In some embodiments, the present invention can be used to treat a subject in need of treatment for chronic kidney disease and/or end-stage renal disease. In some embodiments, the present invention can be used to treat a subject in need of treatment for one or more disorders of phosphate metabolism and/or impaired phosphate transport function.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

DETAILED DESCRIPTION OF THE INVENTION

The present invention provides compositions and methods for removing phosphate from a subject based on phosphate-binding magnesium salts. In some embodiments, the present invention provides compositions and methods for treating hyperphosphatemia using a phosphate-binding magnesium salt or, a combination of phosphate-binding magnesium and calcium salts.

Various aspects of the invention are described in detail in the following sections. The use of sections is not meant to limit the invention. Each section can apply to any aspect of the invention. In this application, the use of "or" means "and/or" unless stated otherwise.

Phosphate-Binding Magnesium Salts

The present invention is, in part, based on the discovery of the unexpected unique features of the phosphate-binding ability of magnesium salts. It was common chemical knowledge that, like many metals (e.g., calcium), the divalent cations of magnesium are capable of forming highly insoluble salts with the phosphate anion in aqueous solutions. However, unlike calcium, the effort of developing therapeutic phosphate-binders based on magnesium salts was not successful before the present invention. As described below, the present inventors discovered that the ability of various magnesium salts to bind phosphate under a condition simulating small intestinal fluid (SIF) is surprisingly different than calcium salts. It was a chemical dogma and theory that if a salt of metallic cations that is more soluble in water than is the corresponding phosphate salt, an insoluble phosphate salt will form when that salt is mixed into a solution containing phosphate. For example, the solubility of calcium chloride in 20° C. water is 745 g/L and the solubility of calcium phosphate is 20 mg/L. Therefore, calcium chloride is 37250 times more soluble in water. When calcium chloride is mixed in water with phosphate, an insoluble calcium phosphate precipitate forms as expected. The solubility of magnesium chloride is 546 g/L in water, and the solubility of magnesium phosphate is 0.26 mg/L. Therefore, magnesium chloride is 2,100,000 times more soluble in water than magnesium phosphate. However, totally unexpectedly and unlike calcium, when a solution of magnesium chloride was mixed with a phosphate solution simulating small intestinal fluid (SIF), no insoluble magnesium phosphate precipitate forms. As described in the Examples section, upon testing numerous magnesium salts for their ability to form insoluble magnesium phosphate in a solution similar to SIF, the inventors of the present application discovered that only a few magnesium salts would effectively precipitate phosphate from SIF. Result from each magnesium salt was unexpected.

In addition, the present inventors further discovered that magnesium salts and calcium salts may interact differently with stomach acid which contains an overwhelming amount of HCl. As described in the Examples section, certain active magnesium salts (e.g., magnesium oxide or hydroxide) may react with stomach acid (HCl) to form magnesium chloride (which, as described above, would not be able to precipitate phosphate in SIF) and thus lose their ability to precipitate phosphate in SIF (see, Example 3). Therefore, it is desirable to enteric coat magnesium salts, in particular, those magnesium salts that are capable of reacting with stomach acid (HCl) (referred to as "active magnesium salts" in this application) such that magnesium salts are protected from stomach acids. Unlike magnesium, calcium salts typically will not lose its ability to precipitate phosphate in SIF after reacting with the stomach acid (HCl) because converted calcium chloride, as described above, readily precipitates phosphate from SIF. Therefore, any calcium salt (acetate, carbonate, etc) absent any enteric coating should still be an effective phosphate binder in humans.

As used herein, the term "phosphate-binding magnesium salts" refers to any magnesium-containing salts that are capable of binding, precipitating, and/or removing phosphate from a mammalian subject under a physiological condition (e.g., in small intestinal fluid) with or without an enteric coating. As used herein, the term "enteric coating" or "enteric film" refers to a barrier applied to, for example, oral medication containing magnesium salts that controls the location in the digestive system where the medication is absorbed. Typically, enteric coatings prevent release of medication before it reaches the small intestine. In some embodiments, enteric coatings suitable for the present invention include surface coatings that are stable at the highly acidic pH (e.g., pH ~3) found in the stomach, but dissolve quickly at a less acidic (relatively more basic) pH (e.g., (above pH 5.5). In some embodiments, phosphate-binding magnesium salts suitable for the invention include magnesium-containing salts that bind at least about 25 mg (e.g., at least about 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg) phosphate per gram of magnesium salt. In some embodiments, the phosphate-binding capacity of a magnesium salt can be characterized using various phosphate-binding assays known in the art. In some embodiments, the phosphate-binding capacity of a magnesium salt is characterized in a solution simulating SIF. Exemplary phosphate-binding assays in solutions simulating SIF are described in the Example sections below. Additional phosphate-binding assays are described in Rosenbaum et al. *Nephrol. Dial. Transplant.* 12:961-964 (1997); and Lowry & Lopez *J. Biol. Chem.* 162:421-428 (1946), the teachings of which are incorporated by reference herein.

Specific phosphate binding capacity of exemplary magnesium salts are described in Example 2 (see Tables 2-5).

In some embodiments, phosphate-binding magnesium salts suitable for the invention include those magnesium salts that bind more than 25 mg phosphate per gram. Such exemplary phosphate-binding magnesium salts include, but are not limited to, magnesium aminobutyrate, magnesium arginate, magnesium aspartate, magnesium betainate, magnesium carnitinate, magnesium glycinate, magnesium hydroxide, magnesium lysinate, magnesium oxide, magnesium propionate, and magnesium tartrate.

In some embodiments, phosphate-binding magnesium salts suitable for the invention include those magnesium salts that bind more than 50 mg phosphate per gram. Such exemplary phosphate-binding magnesium salts include, but are not limited to, magnesium aminobutyrate, magnesium arginate, magnesium aspartate, magnesium betainate, magnesium carnitinate, magnesium glycinate, magnesium hydroxide, magnesium lysinate, magnesium oxide, and magnesium propionate.

In some embodiments, phosphate-binding magnesium salts suitable for the invention include those magnesium salts that bind more than 100 mg phosphate per gram. Such exemplary phosphate-binding magnesium salts include, but are not limited to, magnesium arginate, magnesium betainate, magnesium carnitinate, magnesium glycinate, magnesium hydroxide, magnesium lysinate, and magnesium oxide.

As described in the Examples section, certain phosphate-binding magnesium salts identified by the present inventors have much higher phosphate binding capacity than those existing commercial phosphate binders, such as PhosLo® (calcium acetate) and Renagel® (sevelamer hydrochloride) (see Example 2). Thus, the present invention provides phosphate-binding magnesium salts that can be used for improved and more effective therapies for hyperphosphatemia.

Phosphate-Binding Calcium Salts

In some embodiments, magnesium salts can be used in combination with phosphate-binding calcium salts. Exemplary calcium salts suitable for the present invention include, but are not limited to, calcium acetate (Phosex®, PhosLo®), calcium aceturate, calcium adipate, calcium alaninate, calcium alginate, calcium aminobutyrate, calcium arginate, calcium ascorbate (Calcichew®, Titralac®), calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium carnitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and mixtures or combination thereof.

The molecule weight and percentage of calcium in certain exemplary calcium salts suitable for the present invention are shown in Table 1.

TABLE 1

Exemplary calcium salts suitable for the invention

| Salt of calcium | MW | Percent Ca |
|---|---|---|
| Acetate | 158.17 | 25.34 |
| Alginate | 195.16 | 10.27 |
| Ascorbate | 390.32 | 10.27 |
| Carbonate | 100.09 | 40.04 |
| Carboxymethylcellulose | 257.23 | 7.79 |
| Carnitinate | 362.5 | 11.06 |
| Chloride | 110.98 | 36.11 |
| Citrate | 498.43 | 24.12 |
| Gluconate | 430.37 | 9.31 |
| Lactate | 218.22 | 18.37 |
| Levulinate | 270.29 | 14.83 |
| Orotate | 350.3 | 11.4 |
| Oxide | 56.08 | 71.47 |
| Pantothenate | 476.54 | 8.41 |
| Propionate | 186.22 | 21.52 |
| D-Saccharate (D-glucarate) | 248.2 | 16.15 |
| Stearate | 607.03 | 6.60 |
| Stearyl-2 lactylate | 895.28 | 4.48 |
| Succinate | 156.15 | 25.67 |
| Sulfate | 136.14 | 29.44 |
| Sulfite | 120.14 | 33.36 |
| Tartrate | 188.15 | 21.30 |

Phosphate-binding magnesium salts may also be used in combination with various other phosphate-binding agents including, but not limited to, phosphate-binding aluminium salts (e.g., aluminium hydroxide (Alucaps®)), lanthanum salts (e.g., lanthanum carbonate (Fosrenol®)), polymers (e.g., sevelamer (Renagel®, Renvela®)), and chitosan.

Treatment of Hyperphosphatemia

Phosphate-binding magnesium salts described herein can be used to bind and/or remove phosphate from a mammalian subject. In particular, phosphate-binding magnesium salts described herein can be used to treat hyperphosphatemia. As used herein, the term "hyperphosphatemia" refers to a higher than normal blood level of phosphorous. In human adults, the normal range for blood phosphorous is approximately 2.5-4.5 mg/dL (i.e., 2.5-4.5 mg/100 mL). Typically, an individual with hyperphosphatemia condition has fasting serum phosphorus concentration higher than 5.0 mg/dL (e.g., higher than 5.5 mg/dL, 6.0 mg/dL, 6.5 mg/dL, or 7.0 mg/dL). Methods for measuring phosphate concentrations are well known in the art. For example, phosphate concentrations can be measured by the method of Lowry and Lopez, *J. Biol. Chem.* 162: 421-428. The hyperphosphatemia condition, especially if present over extended periods of time, leads to severe abnormalities in calcium and phosphorus metabolism and can be manifested by aberrant calcification in joints, lungs, and eyes.

Hyperphosphatemia is associated with various diseases or medical conditions including, but not limited to, diseases associated with inadequate renal function such as, for example, chronic kidney disease and/or end-stage renal disease, hypoparathyroidism, and other disorders of phosphate metabolism and/or impaired phosphate transport function.

Typically, a method of treating hyperphosphatemia includes administering to a subject in need of treatment a therapeutically effective amount of a phosphate-binding magnesium salt. In some embodiments, a method of treating hyperphosphatemia includes administering to a subject in need of treatment a therapeutically effective amount of at least one phosphate binding magnesium salt and at least one phosphate-binding calcium salt. As used herein, the term "therapeutically effective amount" refers to an amount effective to reduce or control serum phosphate level or to treat, prevent, and/or delay the onset of the symptom(s) caused by hyperphosphatemia when administered in a single dose or in a series of doses separated by appropriate time intervals, such as hours or days, to a subject suffering from or susceptible to a disease, disorder, and/or condition associated with hyperphosphatemia. A therapeutically effective amount is commonly administered in a dosing regimen that may comprise multiple unit doses. An appropriate unit dose within an effective dosing regimen is referred to as "therapeutically effective dose."

As used herein, an "individual," "patient" or "subject" being treated includes a human or a non-human such as, a non-human mammalian subject including, but not limited to, a bovine, cat, dog, ferret, gerbil, goat, guinea pig, hamster, horse, mouse, nonhuman primate, pig, rabbit, rat, or sheep. As used herein, a "subject susceptible to" a disease, disorder and/or condition associated with hyperphosphatemia refers to an individual at risk of developing hyperphosphatemia or to a patient reporting one or more of the physiological symptoms of hyperphosphatemia, even though a diagnosis of hyperphosphatemia may not have been made.

As used herein, the term "reduce," "decrease," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same condition of hyperphosphatemia as the individual being treated.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of hyperphosphatemia or of a particular disease, disorder, and/or condition underlying hyperphosphatemia. Treatment may be administered to a subject who does not exhibit signs of a disease and/or exhibits only early signs of the disease for the purpose of decreasing the risk of developing pathology associated with the disease. For prophylactic benefit, a composition of the invention may be administered to a patient at risk of developing hyperphosphatemia or to a patient reporting one or more of the physiological symptoms of hyperphosphatemia, even though a diagnosis of hyperphosphatemia may not have been made.

The actual amount effective for a particular application will depend on the condition being treated (e.g., the disease or disorder and its severity, and the age and weight of the patient to be treated) and the route of administration. Determination of an effective amount is well within the capabilities of those skilled in the art, especially in light of the disclosure herein. For example, the effective amount for use in humans can be determined from animal models. For example, a dose for humans can be formulated to achieve circulating and/or gastrointestinal concentrations that have been found to be effective in animals.

Pharmaceutical Compositions

Phosphate-binding magnesium salts may be formulated in a pharmaceutical composition as described herein. When a magnesium salt is used in combination with one or more other phosphate-binding agents, the magnesium salt and the one ore more other phosphate-binding agents can be formulated into one composition or into separate compositions. In some embodiments, a pharmaceutical composition according to the invention contains at least one magnesium salt described herein and at least one calcium salt described herein. Magnesium salt and calcium salt may be combined at various mass or molar ratios. For example, the mass or molar ratio of the calcium salt to the magnesium salt can be between about 100:1 and about 1:100 (e.g., between about 50:1 and about 1:50, between about 20:1 and about 1:20, between about 10:1 and about 1:10, between about 5:1 and about 1:5, between about 3:1 and about 1:3, between about 2:1 and about 1:2, between about 3:2 and about 2:3, between about 5:4 and about 4:5). In some embodiments, the mass or molar ratio of the calcium salt to the magnesium salt is about 1:1. In some embodiments, the mass or molar ratio of the calcium salt to the magnesium salt is about 10:9. In some embodiments, the mass or molar ratio of the calcium salt to the magnesium salt is about 9:10.

Typically, a composition according to the invention is formulated to contain a therapeutically effective amount or dose of magnesium or calcium salt. The actual amount or dose effective for a particular application will depend on the condition being treated (e.g., the disease or disorder and its severity, and the age and weight of the patient to be treated) and the route of administration. Determination of an effective amount or dose is well within the capabilities of those skilled in the art, especially in light of the disclosure herein. For example, the effective amount or dose for use in humans can be determined from animal models. In some embodiments, a dose for humans can be formulated to achieve circulating and/or gastrointestinal concentrations that have been found to be effective in animals.

In some embodiments, a therapeutically effective dose of a calcium salt according to the invention may contain about 20 mg to 1200 mg of calcium (e.g., about 20 mg to about 1000 mg of calcium, about 20 mg to about 800 mg of calcium, about 20 mg to about 600 mg of calcium, about 20 mg to about 400 mg of calcium, about 20 mg to about 200 mg of calcium, about 100 mg to about 300 mg of calcium, about 100 mg to about 500 mg of calcium, about 100 mg to about 700 mg of calcium, about 100 mg to about 900 mg of calcium). In some embodiments, a therapeutically effective dose of a calcium salt according to the invention contains less than about 2000 mg (e.g., less than about 1800 mg, less than about 1600 mg, less than about 1400 mg, less than about 1200 mg, less than about 1000 mg, less than about 800 mg, less than about 600 mg, less than about 500 mg, less than about 400 mg, less than about 300 mg, less than about 200) of calcium. In some embodiments, a therapeutically effective dose of a magnesium salt according to the invention may contain about 20 mg to 1200 mg of magnesium (e.g., about 20 mg to about 1000 mg of magnesium, about 20 mg to about 800 mg of magnesium, about 20 mg to about 600 mg of magnesium, about 20 mg to about 400 mg of magnesium, about 20 mg to about 200 mg of magnesium, about 100 mg to about 300 mg of magnesium, about 100 mg to about 500 mg of magnesium, about 100 mg to about 700 mg of magnesium, about 100 mg to about 900 mg of magnesium). In some embodiments, a therapeutically effective dose of a magnesium salt contains less than about 1200 mg of magnesium (e.g., less than about 1000 mg of magnesium, less than about 800 mg magnesium, less than about 600 mg of magnesium, less than about 400 mg of magnesium, or less than about 200 mg magnesium).

In some embodiments, compositions according to the invention, when administered according to a suitable dosing regimen, provide a therapeutically effective amount of calcium ranging from about 60 mg to about 4000 mg (e.g., from about 80 mg to about 3000, from about 1000 mg to about 2000 mg, from about 500 mg to about 1200 mg, from about 500 mg to about 1100 mg, from about 500 mg to about 1000 mg) per day. In some embodiments, compositions according to the invention, when administered according to a suitable dosing regimen, provide less than about 2000 mg (e.g., less than about 1800 mg, less than about 1600 mg, less than about 1400 mg, less than about 1200 mg, less than about 1000 mg, less than about 800 mg, less than about 600 mg, less than about 400 mg, or less than about 200 mg) calcium per day. In some embodiments, compositions according to the invention, when administered according to a suitable dosing regimen, provide a therapeutically effective amount of magnesium ranging from about 60 mg to about 4000 mg (e.g., from about 80 mg to about 3000, from about 1000 mg to about 2000 mg, from about 500 mg to about 1200 mg, from about 500 mg to about 1100 mg, from about 500 mg to about 1000 mg) per day. In some embodiments, compositions according to the invention, when administered according to a suitable dosing regimen, provide more than about 500 mg (e.g., more than about 750 mg, more than about 1000 mg, more than about 1250 mg, more than about 1500 mg, more than about 1750 mg, or more than about 2000 mg) magnesium per day. In some embodiments, compositions according to the invention, when administered according to a suitable dosing regimen, provide less than about 4000 mg (e.g., less than about 3500 mg, less than about 3000 mg, less than about 2500 mg, less than about 2000 mg, less than about 1500 mg, or less than about 1000 mg) magnesium per day.

Compositions according to the invention may be administered four times a day, three times a day, twice a day, once daily, once every other day, twice a week, or once a week. In some embodiments, compositions according to the invention may be administered together with a meal.

Typically, a composition of the invention further includes a carrier. A carrier suitable for the invention is also referred to as a pharmaceutically acceptable carrier, a carrier-diluent, or excipient. A carrier may be a solid, semi-solid or liquid material which acts as an excipient, medium, and/or vehicle for chitosan. For example, a composition of the invention can be in a solid or liquid medium. For example, phosphate-binding salts may be enclosed within a carrier, such as a capsule, paper, sachet or other container. In particular, a suitable carrier, excipient, or diluent may be a starch, a gum, an alginate, a silicate, dextrose, gelatin, lactose, mannitol, sorbitol, sucrose, tragacanth, cellulose, methyl cellulose, microcrystalline cellulose, a methylhydroxybenzoate, a propylhydroxybenzoate, polyvinylpyrrolidone or talc.

A composition of the invention can be formulated for administration by injection, topically, orally, transdermally, or rectally. In some embodiments, a composition of the present invention is formulated for oral administration. For example, a composition according to the invention may be in a form of a cachet, a hard gelatin capsule, a soft gelatin capsule, an elixir, a lozenge, a pill, a powder, a sachet, a sterile packaged powder, a suspension, a syrup, a tablet, a capsule, solution, or emulsion, to name but a few.

In some embodiments, a composition according to the invention may contain an enteric coating or film. Such a formulation or composition is also referred to as an "enterically coated" formulation or composition. As used herein, the term "enteric coating" or "enteric film" refers to a barrier applied to, for example, oral medication that controls the location in the digestive system where the medication is absorbed. Typically, enteric coatings prevent release of medication before it reaches the small intestine. In some embodiments, enteric coatings suitable for the present invention include surface coatings that are stable at the highly acidic pH (e.g., pH ~3) found in the stomach, but dissolve quickly at a less acidic (relatively more basic) pH (e.g., (above pH 5.5). According to the present invention, an enteric film or coating prevents dispersion of magnesium salt and/or calcium salt in the acidic environment of the lumen of the stomach. Materials suitable for enteric coatings include, but not limited to, acetyltributyl citrate, carbomers, cellulose acetate phthalate, cellulose acetate succinate, ethyl cellulose, fatty acids, guar gum, hypromellose acetate succinate, hypromellose phthalate, polymethacrylates, polyvinyl acetate phthalate, plastics, shellac, tributyl citrate, triethyl citrate, waxes (e.g., white wax), zein and combination thereof.

In some embodiments, a composition of the invention can be a food, a drink, or a nutritional, food or dietary supplement. In one embodiment, the composition is a nutritional supplement. As used herein, "a nutritional supplement" is a preparation formulated to supply nutrients (including, but not limited to, vitamins, minerals, fatty acids or amino acids) that are missing or not consumed in sufficient quantity in a person's or animal's diet. As used in this application, a nutritional supplement is also referred to as "a food supplement" or "a dietary supplement."

In some embodiments, the composition of the invention is a nutritional supplement for a person's diet. The nutritional supplement can be administered with or without meals and can be administered once daily, twice daily, three times daily, once every other day, twice a week, once a week, or at a variable intervals. In some embodiments, the nutritional supplements can be administered three times daily with meals. Supplements may be in various forms including, for example, powders, liquids, syrups, pills, encapsulated compositions, etc.

In some embodiments, the composition of the invention is a nutritional supplement for an animal's diet, such as, a feed or pet food used with another feed or pet food to improve the nutritive balance or performance of the total. Contemplated supplements include compositions that are fed undiluted as a supplement to other feeds or pet foods, offered ad libitum with other parts of an animal's ration that are separately available, or diluted and mixed with an animal's regular feed or pet food to produce a complete feed or pet food.

In another embodiment, a composition of the invention can be a treat for animals. Treats include, for example, compositions that are given to an animal to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic.

Typically, phosphate-binding magnesium salts are present in the composition at concentrations that do not impart an odor or flavor that causes the intended animal to perceive the composition to be unacceptable for consumption. In many instances, a desirable odor and flavor can be achieved using aroma or flavor enhancers.

In some embodiments, the percentage of the magnesium salt(s) or the combined mass of magnesium and calcium slats, in a composition of the invention is at least about 0.005% by weight of the composition (e.g., at least about 0.1%, 0.5%, 1.0%, 1.5%, 2%, 2.5%, 3%, 3.5%, 4%, 4.5%, 5%, 10%, 15%, 20%, 25%, 30% or higher). In some embodiments, the percentage of magnesium and/or calcium salts in a composition of the invention ranges from about 0.1% to about 30% based on the weight of the composition. In some embodiments, the percentage of magnesium and/or calcium salts in a composition of the invention ranges from about 0.1% to about 10% based on the weight of the composition. In some embodiments, the percentage of magnesium and/or calcium salts in a composition of the invention ranges from about 0.2% to about 5% based on the weight of the composition. In some embodiments, the percentage of magnesium and/or calcium salts in a composition of the invention ranges from about 0.35% to about 1.0% based on the weight of the composition.

The present invention, thus generally described, will be understood more readily by reference to the following examples, which are provided by way of illustration and are not intended to be limiting of the present invention.

EXAMPLES

Example 1

Phosphate-Binding Assays

Exemplary stock solutions suitable for phosphate-binding assays include the following: phosphate-binding solution ("PBS") containing 10 mM $KH_2PO_4$, 30 mM $Na_2CO_3$, 80 mM NaCl, as described in Rosenbaum et al. *Nephrol. Dial. Transplant.* 12:961-964 (1997); acetate buffer ("AB") solution containing 0.1N acetic acid, 0.025N sodium acetate, as described in Lowry & Lopez *J. Biol. Chem.* 162:421-428 (1946); ammonium molybdate ("AM") solution containing 1% ammonium molybdate in 0.05N $H_2SO_4$, as described in Lowry & Lopez; ascorbic acid ("AA") solution containing 1% ascorbic acid in $H_2O$, as described in Lowry & Lopez.

In general, the phosphate-binding assay was conducted in 12×75 mm glass tubes. 4.0 mL PBS (which is a solution simulating SIF) and 20 mg putative phosphate binder were added to a glass tube and then mixed for 1 h at room temperature. 0.1 mL supernatant was pipetted from this tube to a new test tube. 3.0 mL AB, 0.3 mL AA and 0.3 mL AM solutions were added and O.D. were measured at 700 nm after 10 minutes. The assay was shown to be linear over the range used in this example.

The phosphate binding capacity was calculated as follows (mcg stands for micrograms):

((O.D. of sample×95)/O.D. of standard)×40=mcgPO4 left in solution ((3800−mcgPO4 left)×50)/1000=mgPO4 bound per gram of phosphate binder

Example 2

Exemplary Phosphate-Binding Magnesium Salts

The phosphate binding capacity of various magnesium and calcium salts were measured using the phosphate-binding assays described in Example 1. Exemplary results were shown in Tables 2-5.

TABLE 2

Exemplary phosphate-binding results

| Sample | $PO_4$ binding, mg/g |
|---|---|
| PhosLo ® | 146.6 |
| MgO | 184.0 |
| Mg(OH)2 | 176.2 |
| MgCO3 | 19.0 |
| MgSO4•7H2O | 19.0 |
| Mg citrate | 16.3 |
| CaCO3 | 10.9 |

TABLE 3

Exemplary phosphate-binding magnesium salts

| Sample | $PO_4$ binding, mg/g |
|---|---|
| PhosLo ® | 171 |
| Renagel ® | 85 |
| Mg acetate | 4 |
| Mg adipate | 6 |
| Mg aminobutyrate | 85 |
| Mg arginate | 121 |
| Mg ascorbate | 4 |
| Mg aspartate | 50 |
| Mg betainate | 147 |
| Mg carbonate | 22 |
| Mg chloride | 4 |
| Mg citrate | 15 |
| Mg carnitinate | 169 |
| Mg formate | 6 |
| Mg fumarate | 4 |
| Mg glycinate | 176 |
| Mg hydroxide | 182 |
| Mg lactate | 15 |
| Mg lysinate | 150 |
| Mg maleate | 15 |
| Mg nicotinate | 4 |
| Mg orotate | 20 |
| Mg oxide | ≥190 |
| Mg propionate | 59 |
| Mg stearate | 15 |
| Mg succinate | 18 |
| Mg sulfate | 9 |
| Mg tartrate | 28 |

Certain phosphate-binding results of Table 3 were calculated to reflect the phosphate-binding capacity as follows.

TABLE 4

Exemplary phosphate-binding capacity

| Compound | % Mg (or % Ca) | mg PO$_4$ bound per g compound | mg PO$_4$ bound per g Mg or Ca in compound |
|---|---|---|---|
| Mg arginate | 6.5 | 121 | 1862 |
| Mg betainate | 9.5 | 147 | 1547 |
| Mg glycinate | 14.1 | 176 | 1248 |
| Mg hydroxide | 41.7 | 182 | 436 |
| Mg lysinate | 7.7 | 150 | 1948 |
| Mg oxide | 60.3 | 190 | 315 |
| PhosLo ® (Ca acetate) | (25.3% Ca) | 171 | 676 |

It can be seen that certain magnesium salts have high phosphate-binding capacity. For example, 1 gram of Mg in some magnesium salts (e.g., Mg lysinate) binds phosphate almost three times as much as 1 gram of calcium in PhosLo® (Ca acetate) does.

Additional results are shown in Table 5.

TABLE 5

Exemplary phosphate-binding capacity

| Compound | mg PO$_4$ bound per g compound | mg PO$_4$ bound per g Mg (or Ca) in compound |
|---|---|---|
| PhosLo(R)(Ca acetate) | 161 | (636, per gram Ca) |
| Mg aminobutyrate | 76 | |
| Mg arginate | 118 | 1815 |
| Mg betainate | 141 | 1484 |
| Mg glycinate | 177 | 1255 |
| Mg lysinate | 138 | 1792 |
| Mg oxide | 187 | 310 |
| Mg malate | 29 | |

Example 3

Impact of Stomach Acid on the Phosphate-Binding Ability of Certain Magnesium Salts This experiment was conducted to demonstrate that stomach acid can destroy the phosphate-binding activity of a normally active magnesium salt. Specifically, 20 mg MgO was first reacted with 100 µL 10M HCl which simulates the overwhelmingly acidic stomach environment. The reacted mixture were then tested for its ability to bind phosphate in an phosphate-binding assay as described above. As shown in Table 6, MgO, which normally has a phosphate-binding capacity of about 188.5 mg/g, lost its ability to bind phosphate after the reaction with 100 µL 10M HCl. Similar results were observed with Mg(OH)2.

TABLE 6

Exemplary results illustrating the impact of stomach acid

| Sample | PO$_4$ binding, mg/g |
|---|---|
| PhosLo ® | 148.8 |
| MgO | 188.5 |
| 20 mg MgO + 100 µL 10M HCl | 0 |
| Mg(OH)2 | 179.0 |
| 20 mg Mg(OH)$_2$ + 70 µL 10M HCl | 0 |

Example 4

Composition Containing Calcium Acetate and Magnesium Glycinate

This experiment was designed to show the therapeutic and nutritional benefits provided by a composition of the invention that contains both calcium and magnesium salts. Specifically, a composition containing both calcium acetate and magnesium glycinate was made by mixing PhosLo® (calcium acetate) and magnesium glycinate at a mass ratio of approximately 1:1 (e.g., 300 mg Mg glycinate and 340 mg Ca acetate). The phosphate binding ability of the composition was determined by the phosphate-binding assay described in Example 1 and exemplary results were shown in Table 7.

TABLE 7

| Compound | PO$_4$ binding, mg/g |
|---|---|
| PhosLo(R) | 152 |
| Mg glycinate | 182 |
| PhosLo:MgGlycinate::1:1 | 185 |

As shown in Table 7, the composition containing both PhosLo® (calcium acetate) and magnesium glycinate binds approximately 185 mg phosphate per gram, which is more effective than PhosLo® alone (which binds approximately 152 mg phosphate per gram) and comparable to Mg glycinate alone (which binds approximately 182 mg phosphate per gram).

A therapeutic composition is made that contains 300 mg Mg glycinate and 340 mg Ca acetate per dose. Under the existing practice, a human patient typically takes four doses of PhosLo® with each meal, three meals a day. Therefore, the patient ingests approximately 2025 mg Ca a day, which would result in the binding of approximately 1328 mg phosphate. If a patient instead takes four doses of the therapeutic composition containing 300 mg Mg glycinate and 340 mg Ca acetate per dose with each meal, three meals a day, the patient would ingest about 1032 mg Ca (which binds about 677 mg phosphate), and about 508 mg Mg (which binds about 635 mg phosphate). Therefore, the composition containing 300 mg Mg glycinate and 340 mg Ca acetate per dose would remove about 1312 mg phosphate per day, similar to the amount of phosphate removed by PhosLo® using the existing treatment method. However, a patient treated with the composition containing 300 mg Mg glycinate and 340 mg Ca acetate will only ingest 1032 mg Ca per day, which is almost only one half of the Ca amount ingested by a patient per day treated by PhosLo®. Moreover, the composition containing 300 mg Mg glycinate and 340 mg Ca acetate per dose provides 508 mg Mg per day, a nutrient deficient in many individuals, while PhosLo® provides 0 mg Mg. Therefore, a therapeutic composition based on a combination of magnesium and calcium salts provides effective phosphate-binding while significantly reducing calcium burdens in patients and, at the same time, providing nutritional benefits.

Example 5

Preparation of an Oral Formulation with an Enteric Coating

An oral formulation that contains calcium acetate and magnesium glycinate is prepared as follows. Calcium acetate, magnesium glycinate, one excipient suitable for enteric coating, one or more pharmaceutically acceptable excipients and other appropriate ingredients (e.g., a lubricant) are mixed until a degree of uniformity suitable for pharmaceutical formulation is reached. The mixture is shaped into tablets or caplets. Tablets or caplets are then coated with at least one excipient suitable for enteric coating using standard methods.

Example 6

Treatment of Hyperphosphatemia

An oral formulation containing calcium acetate and magnesium glycinate prepared as described in Example 5 is used to treat human patients suffering from hyperphosphatemia. The first patient has a serum phosphorus level between about 5.5 and about 7.5 mg/dL and has not taken a phosphate binder. Two units of the formulation are orally administered to the patient three times daily with meals. The second patient has a serum phosphorus level between about 7.5 and about 9.0 mg/dL and has not taken a phosphate binder. Three units of the same formulation are orally administered to the patient three times daily with meals. The third patient has a serum phosphorus level greater than about 9.0 mg/dL and has not taken a phosphate binder. Four units of the formulation are orally administered to the patient three times daily with meals. The fourth patient has been taking one 667-mg calcium acetate tablet per meal. One unit of the formulation is orally administered to the fourth patient three times daily with meals, instead of the one 667-mg calcium acetate tablet per meal. The fifth patient has been taking two 667-mg calcium acetate tablets per meal. Two units of the formulation are orally administered to the patient three times daily with meals, instead of the two 667-mg calcium acetate tablets per meal. The sixth patient has been taking three 667-mg calcium acetate tablets per meal. Three units of the formulation are orally administered to the patient three times daily with meals, instead of the three 667-mg calcium acetate tablets per meal.

In each of the above cases, the patient's serum phosphorus level is reduced to and remains in the range from 3.5 to 5.5 mg/dL after treatment according to the dosing regimen described above. A dosing regimen can be maintained relatively unchanged when the serum phosphorus level is within the range of 3.5 to 5.5 mg/dL.

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description are introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION OF REFERENCES

All publications and patent documents cited in this application are incorporated by reference in their entirety to the same extent as if the contents of each individual publication or patent document were incorporated herein.

What is claimed is:

1. A composition suitable for treating hyperphosphatemia comprising a therapeutically effective dose of at least one calcium salt and at least one phosphate-binding magnesium salt, wherein the at least one phosphate-binding magnesium salt comprises magnesium glycinate, and wherein the composition is formulated for oral administration and the composition comprises an enteric coating.

2. The composition of claim 1, wherein the magnesium glycinate binds at least about 50 mg phosphate per gram.

3. The composition of claim 1, wherein the therapeutically effective dose of at least one calcium salt comprises about 20 mg to 1200 mg of calcium.

4. The composition of claim 1, wherein the at least one calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium camitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combination thereof.

5. The composition of claim 1, wherein the mass ratio of the at least one calcium salt to the at least one phosphate-binding magnesium salt is between about 100:1 and about 1:100.

6. The composition of claim 1, wherein the mass ratio of the at least one calcium salt to the at least one phosphate-binding magnesium salt is between about 5:4 and about 4:5.

7. The composition of claim 6, wherein the mass ratio of the at least one calcium salt to the at least one phosphate-binding magnesium salt is about 1:1.

8. The composition of claim 1, wherein the at least one calcium salt comprises calcium acetate.

9. The composition of claim 8, wherein the therapeutically effective dose of calcium acetate is about 340 mg and the therapeutically effective dose of magnesium glycinate is about 300 mg.

10. The composition of claim 1, wherein the composition is in a form of a tablet, a cachet, a hard gelatin capsule, a soft gelatin capsule, a lozenge, suspension, or a bead.

11. A composition suitable for treating hyperphosphatemia comprising a therapeutically effective dose of at least one phosphate-binding magnesium salt, wherein the at least one phosphate-binding magnesium salt binds at least about 50 mg phosphate per gram, wherein the composition is formulated for oral administration and the composition comprises an enteric coating.

12. The composition of claim 11, wherein the at least one phosphate-binding magnesium salt binds at least about 100 mg phosphate per gram.

13. The composition of claim 11, wherein the at least one phosphate-binding magnesium salt is not magnesium carbonate.

14. The composition of claim 11, wherein the at least one phosphate-binding magnesium salt is selected from the group consisting of magnesium aminobutyrate, magnesium arginate, magnesium aspartate, magnesium betainate, magnesium camitinate, magnesium glycinate, magnesium hydroxide, magnesium lysinate, magnesium oxide, magnesium propionate, and combination thereof.

15. The composition of claim 11, wherein the therapeutically effective dose of at least one phosphate-binding magnesium salt comprises about 20 mg to 1200 mg magnesium.

16. The composition of claim 11, wherein the composition is in a form of a tablet, a cachet, a hard gelatin capsule, a soft gelatin capsule, a lozenge, suspension, or a bead.

17. A method of treating hyperphosphatemia comprising administering to a subject in need of treatment the composition of claim 1.

18. A method of treating hyperphosphatemia comprising administering to a subject in need of treatment a calcium salt and a phosphate-binding magnesium salt, wherein the phosphate-binding magnesium salt comprises magnesium glycinate.

19. A method of treating hyperphosphatemia comprising administering to a subject in need of treatment a composition of claim 11.

20. The composition of claim 11, further comprising at least one calcium salt.

21. The composition of claim 20, wherein the at least one calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium camitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combinations thereof.

22. The composition of claim 20, wherein the at least one calcium salt comprises calcium acetate.

23. The method of claim 18, wherein the calcium salt is selected from the group consisting of calcium acetate, calcium aceturate, calcium adipate, calcium alaninate, calcium alginate, calcium aminobutyrate, calcium arginate, calcium ascorbate, calcium aspartate, calcium benzoate, calcium besylate, calcium betainate, calcium bromide, calcium buteprate, calcium butyrate, calcium caproate, calcium carbesilate, calcium carbonate, calcium carboxymethylcellulose, calcium camitinate, calcium chloride, calcium ciclotate, calcium citrate, calcium cypionate, calcium enanthate, calcium esylate, calcium ethandisulfonate, calcium formate, calcium fumarate, calcium glucarate, calcium gluceptate, calcium gluconate, calcium glucuronate, calcium glutamate, calcium glycinate, calcium hippurate, calcium hyclate, calcium hydroxide, calcium iodide, calcium isethionate, calcium lactate, calcium lactobionate, calcium levulinate, calcium lysinate, calcium malate, calcium maleate, calcium mesylate, calcium metilsulfate, calcium methylsulfate, calcium naphthoate, calcium napsylate, calcium nicotinate, calcium nitrate, calcium oleate, calcium orotate, calcium oxide, calcium oxoglurate, calcium pamoate, calcium pantothenate, calcium picolinate, calcium pivalate, calcium polygalacturonate, calcium propionate, calcium sorbate, calcium steaglate, calcium stearate, calcium stearyl-2-lactylate, calcium succinate, calcium sulfate, calcium sulfite, calcium tartrate, calcium tebutate, calcium tosylate, calcium triflutate, calcium xinafoate, and combinations thereof.

24. The method of claim 18, wherein the calcium salt comprises calcium acetate.

* * * * *